United States Patent [19]
Van Veen

[11] Patent Number: 5,379,770
[45] Date of Patent: Jan. 10, 1995

[54] METHOD AND APPARATUS FOR TRANSCRANIAL DOPPLER SONOGRAPHY

[75] Inventor: Barry D. Van Veen, McFarland, Wis.

[73] Assignee: Nicolet Biomedical, Inc., Madison, Wis.

[21] Appl. No.: 172,594

[22] Filed: Dec. 21, 1993

[51] Int. Cl.$^6$ ............................................. A61B 8/06
[52] U.S. Cl. ............................................. 128/661.09
[58] Field of Search .................. 128/661.07–661.10; 73/861.25; 364/413.25

[56] References Cited

U.S. PATENT DOCUMENTS 4,770,184  9/1988  Greene, Jr. et al. ............ 128/661.08

OTHER PUBLICATIONS

Knox, R. A. et al "Computer Based Classification of Carotid Arterial Disease: A Prospective Assessment" *Stroke* vol. 13, No. 5 Sep.–Oct. 1982 pp. 589–594.
David J. Thomson, "Spectrum Estimation and Harmonic Analysis", Proceedings of the IEEE, vol. 70, No. 9, Sep. 1982, pp. 1055–1096.
R. Aaslid, "The Doppler Principle Applied to Measurement of Blood Flow Velocity in Cerebral Arteries," Chap. 3, pp. 22–38, in Transcranial Doppler *Sonography*(book), R. Aaslid, Ed., Springer-Verlag, Wien, New York, 1986.
Thomas P. Bronez, "Spectral Estimation of Irregularly Sampled Multi-dimensional Processes by Generalized Prolate Spheroidal Sequences," IEEE Trans. on Acoustics, Speech, and Signal Processing, vol. 36, No. 12, Dec. 1988, pp. 1862–1873.
N. Levanon, *Radar Principles* (book), Chap. 10, "Processing a Coherent Pulse Train", pp. 202–218, Wiley Inter-Science 1988.
Barry C. Van Veen, et al., "Estimation of Structured Covariance Matrices and Multiple Window Spectrum Analysis," IEEE Trans. on Acoustics, Speech, and Signal Processing, vol. 38, No. 8, Aug. 1990, pp. 1467–1472.
C. T. Mullis, et al., "Quadratic Estimators of the Power Spectrum," Chap. 1, pp. 1–57, in *Advances in Spectrum Analysis and Array Processing*, vol. 1 (book), S. Haykin, Ed., Prentice Hall, Englewood Cliffs, N.J., 1991.
Tsung-Ching Liu, et al., "Multiple Window Based Minimum Variance Spectrum Estimation for Multidimensional Random Fields," IEEE Trans. on Signal Processing, vol. 40, No. 3, Mar. 1992, pp. 578–589.
A. Drosopoulos, et al., "Adaptive Radar Parameter Estimation with Thomson's Multiple-Window Method," Chap. 7, pp. 381–461, in *Adaptive Radar Detection and Estimation*, S. Haykins, et al., Eds., Wiley, New York, 1992.
TC 2000S Transcranial Doppler System Service Handbook, Eden Medizinische Elektronik, GmbH, Aug. 1990.
TC 2000 Transcranial Doppler System Operator's Handbook, Eden Medical Electronics, GmbH, May 1992.

*Primary Examiner*—Francis Jaworski
*Attorney, Agent, or Firm*—Foley & Lardner

[57] ABSTRACT

The effect of noise in the displayed information obtained from transcranial Doppler measurements is reduced by estimating the spectra of the returned Doppler signal as the average of Fourier spectra computed using multiple windows for the data being analyzed. The windows are chosen so that the spectra from different windows are approximately statistically independent, thereby reducing the variance of the spectrum by the averaging process. The Doppler data may be obtained by applying repeated pulses of ultrasonic energy to the head of a subject and isolating the Doppler frequency components of the return signal to obtain a set of data from a selected number of pulses. The data set so obtained has the multiple window functions applied thereto to obtain multiple windowed data sets which are operated on, as in a digital signal processor, to obtain multiple discrete Fourier transforms of the windowed data sets. A power spectrum is estimated as the averaged sum of the squares of the magnitudes of each of the discrete Fourier transforms. The spectra obtained from data sets gathered in sequence may be displayed to an operator to show the spectral content of the return signal over time, which corresponds to the velocity of blood flow at a position within the head of the subject as a function of time.

13 Claims, 9 Drawing Sheets

METHOD AND APPARATUS FOR TRANSCRANIAL DOPPLER SONOGRAPHY

FIELD OF THE INVENTION

This invention pertains generally to the field of medical instrumentation for carrying out cerebrovascular investigations and diagnoses, and particularly to transcranial Doppler instruments.

BACKGROUND OF THE INVENTION

In the ultrasound measurement of blood flow, a hand held or headpiece mounted probe is typically used to transmit a pulsed beam of ultrasound through body tissue to a focal point within a target artery. Blood cells flowing through the artery, being denser than surrounding tissue, scatter the ultrasound in many directions. A portion of the transmitted ultrasound is reflected directly back to the probe, which can then function as a receiver.

In accordance with the well known Doppler phenomenon, an observer in motion relative to a wave source will receive a wave from the source which has a frequency different than the frequency of the wave at the source. If the source is moving toward the observer, a higher frequency wave is received by the observer, and, conversely, if the wave source is moving away from the observer, a lower frequency wave is received. The difference between the emitted and received frequencies is known as the Doppler shift.

Instruments have been developed to obtain noninvasive measurements of blood velocity in interior arteries and veins using Doppler principles. One instrument in present use for obtaining transcranial Doppler measurements is the TC 2000S Transcranial Doppler System available from the EME (Eden Medizinische Electronik GmbH) division of Nicolet Instrument Corporation. The operation of such instruments in accordance with the Doppler principle may be illustrated with respect to FIGS. 1–4. In FIG. 1, the ultrasound probe 40 acts as a stationary wave source, emitting pulsed ultrasound at a frequency of, e.g., 2 MHz. This ultrasound is transmitted through the skull 41 and the tissue of the brain to a blood vessel 42. For purposes of illustration, a blood cell 43 is shown moving toward the probe and acts as a moving observer. As illustrated in FIG. 2, the blood cell reflects the pulse of ultrasound and can be considered a moving wave source. The probe receives this reflected ultrasound, acting as a stationary observer. The frequency of the ultrasound received by the probe, $f_1$, is higher than the frequency, $f_0$, originally emitted. The Doppler shift of the received wave can then be calculated. FIG. 3 shows the effect on a pulse of ultrasound when blood flows in a direction away from the probe. In this case, the received frequency, $f_2$, reflected from the blood cell, is lower than the emitted frequency $f_0$. Again, the Doppler shift can be calculated.

The Doppler effect can be used to determine the velocity of blood flow in the cerebral arteries. For this purpose, the Doppler equation used is the following:

$$F_d = \frac{2 \times F_t \times V \times \cos\theta}{V_0}$$

where:
$F_d$ = Doppler frequency shift
$F_t$ = Frequency of the transmitter
$V$ = Velocity of blood flow
$\theta$ = Angle of incidence between the probe and the artery
$V_0$ = Velocity of ultrasound in body tissue Typically, $F_t$ is a constant, e.g., 2, 4 or 8 MHz, and $V_0$ is approximately 1540 meters per second (m/s) in soft body tissue.

Assuming that there is a zero angle of incidence between the probe and the artery, the value of cos θ is equal to 1. The effect of the angle θ is only significant for angles of incidence exceeding 30°.

In the TC 2000S System, ultrasonic energy is provided in bursts at a pulse repetition rate or frequency. The probe receives the echoes from each burst and converts the sound energy to an electrical signal. To obtain signal data corresponding to reflections occurring at a specific depth (range) within the head, an electronic gate opens to receive the reflected signal at a selected time after the excitation pulse, corresponding to the expected time of arrival of an echo from a position at the selected depth. The range resolution is generally limited by the bandwidth of the various components of the instrument and the length of the burst. The bandwidth can be reduced by filtering the received signal, but at the cost of an increased length of sample volume.

Other body movements, for example, vessel wall contractions, can also scatter ultrasound which will be detected as "noise" in the Doppler signal. To reduce this noise interference, a high pass filter is used to reduce the low frequency, high amplitude signals. The high pass filter typically can be adjusted to have a passband above a cutoff frequency selectable between 0 and, e.g., 488 Hz.

Because not all blood cells in the sample volume are moving at the same speed, a range or spectrum of Doppler shifted frequencies are reflected back to the probe. Thus, the signal from the probe 40 may be converted to digital form by an analog-to-digital converter, and the spectral content of the sampled Doppler signal calculated by a computer or digital signal processor using a fast Fourier transform method. This processing method produces a velocity profile of the blood flow, which varies over the period of a heartbeat. The process is repeated to produce a beat-to-beat flow pattern, or sonogram, on a video display. The TC 2000S instrument can be configured to analyze 64 or 128 separate frequency ranges within the spectrum of Doppler signals. Color coding may be used to show the intensity of the signal at different points on the spectral line. The intensity of the signal will represent the proportion of blood cells flowing within that particular velocity range. The information displayed on the video screen can be used by a trained observer to determine blood flow characteristics at particular positions within the brain of the individual being tested, and can detect anomalies in such blood flow, for example, the possible presence of a blockage or restriction, or the passage of an embolus through the artery which introduces a transient distortion of the displayed information. The TC 2000S also includes a processing option which provides a maximum frequency follower or envelope curve which is displayed on the video screen as the white outline of the flow spectrum.

The usefulness of the information obtained with such transcranial Doppler instruments can be affected if significant noise is present. It is therefore desirable to improve the signal-to-noise ratio (SNR) of the received data in a manner which does not significantly compromise the desired signal data which is representative of blood flow velocity. A better spectral display can sometimes be obtained by performing many fast Fourier transforms (FFT) on the data and averaging these to reduce the random fluctuations of the spectral amplitudes or by performing a sliding FFT on overlapping data sets and averaging several of these FFTs. The background noise is reduced somewhat in this manner, which facilitates tracing of the spectral outline, but significant noise is often present which it is desirable to further reduce.

SUMMARY OF THE INVENTION

In accordance with the invention, a method and apparatus are provided for reducing the effect of noise in the displayed spectra obtained from transcranial Doppler measurements. The invention estimates the spectrum of the return Doppler signal as an average of Fourier spectra computed using different windows applied to the data being analyzed. The windows are chosen so that the spectra from different windows are approximately statistically independent. The variance of the spectrum is thus significantly reduced by this averaging process.

In the present invention, a pulse of ultrasound energy is applied to the head of an individual by a probe, and the ultrasound energy received by the probe is converted to an electrical signal. The signal is mixed with a signal at the transmitted frequency to isolate the Doppler frequency components from the received signal. The isolated components are sampled to provide digital data. This process is repeated at the pulse repetition rate to provide a set of digital data. The power spectrum is determined for the set of digital data by providing multiple window weighting functions for the data set, with each of the window functions determined so that the power spectra associated with different windows are approximately statistically independent. Each of the window functions is then applied to the data set and a discrete Fourier transform is performed on each of the windowed data sets. The power spectrum is determined as the averaged sum of the squares of the magnitudes of each of the discrete Fourier transforms. New data sets are collected from later groups of pulses, and the process repeated, to provide a power spectra as a function of time. The power spectra may then be displayed on a video screen to an operator in a conventional manner, for example, as a spread of illuminated points with the concentration of points being related to the energy density at particular frequencies (and thus, to blood flow velocities). The power spectra displayed will vary from heartbeat to heartbeat as a function of time progressing along the horizontal axis.

The multiple window spectrum estimate is preferably determined as the average of the magnitude squared of windowed discrete Fourier transforms of the data, i.e., for "M" windows as:

$$S_{MW}(f) = \frac{1}{M} \sum_{m=1}^{M} \left| \sum_{k=0}^{N-1} v_m(k) \times (k) e^{-j2\pi fk} \right|^2.$$

where $v_j(k)$ is k th element of the j th window function, $x(k)$ is the k th element of the data set, $k=0, 1, 2, \ldots, N-1$, and N is the record length of the data set.

In accordance with the present invention, many different methods can be used to determine the window functions. In the preferred window selection method, the parameters determining the data windows can be selected by the user to provide a desired stability of the spectral estimate while maintaining a desired level of resolution. Generally, a user may specify a main lobe width, 2B (in Hz normalized on a frequency range $-0.5 < F \leq 0.5$), which may be viewed as the resolution limit of the estimator since spectral details that occur on a finer scale cannot be seen in the spectral estimate. The main lobe width also determines the maximum number of windows and the maximum number of windowed discrete Fourier transforms that can be averaged. If N is the record length of the data set, then the absolute maximum number of windows that can be used is 2NB, with a practical upper limit of about 2NB−2. Such windows can be determined, for example, in accordance with Thompson's multiple window method, for example, by constructing an N×N matrix Q having the entries as follows:

$$Q_{mn} \begin{cases} 2B, \\ \sin[2\pi B(m-n)]/[\pi(m-n)], \\ m = n \\ m, n = 0, 1, \ldots, N-1 \text{ and } m \neq n \end{cases}$$

The eigenvectors $v_j$ of the matrix Q are then determined in accordance with the expression (where $\lambda_j$ are the eigenvalues):

$$Qv_j = \lambda_j v_j, j = 1, 2, \ldots, N.$$

The eigenvectors so calculated provide the window functions for the averaging process. The first few eigenvalues of the matrix Q are approximately 1, and the eigenvalues drop off rapidly to approximately 0 thereafter. Generally, only the first few eigenvectors are used as data windows because the closer the eigenvalue is to unity, the smaller will be the sidelobes of the window.

The spectral estimates determined in accordance with the present invention have significantly less background noise than estimates determined using discrete Fourier transforms with simple windows (e.g., rectangular or quasi-rectangular), and constitute an improvement over conventional averaging of multiple discrete Fourier transform estimates. Further, because of the sharpness of the frequency responses, relatively little distortion of the actual received pulse signal data occurs. The better signal to noise ratio obtained with the present invention allows better envelope tracing of the displayed data, lower power transmitted to the subject, and the extension of transcranial Doppler measurements to subjects that have been difficult to measure, e.g., those having unusually thick skulls.

Further objects, features and advantages of the invention will be apparent from the following detailed description when taken in conjunction with the accompanying drawings.

DETAILED DESCRIPTION OF THE INVENTION

Figure 1:
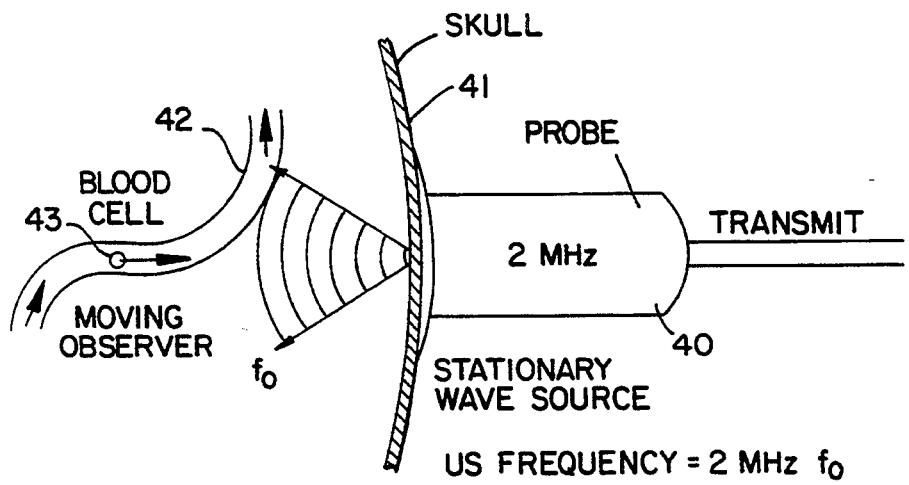
FIGS. 1–4 are illustrative views showing the manner in which ultrasonic pulses are applied to the head of an individual to obtain information on the velocity of blood flowing in an interior blood vessel.
Figure 2:
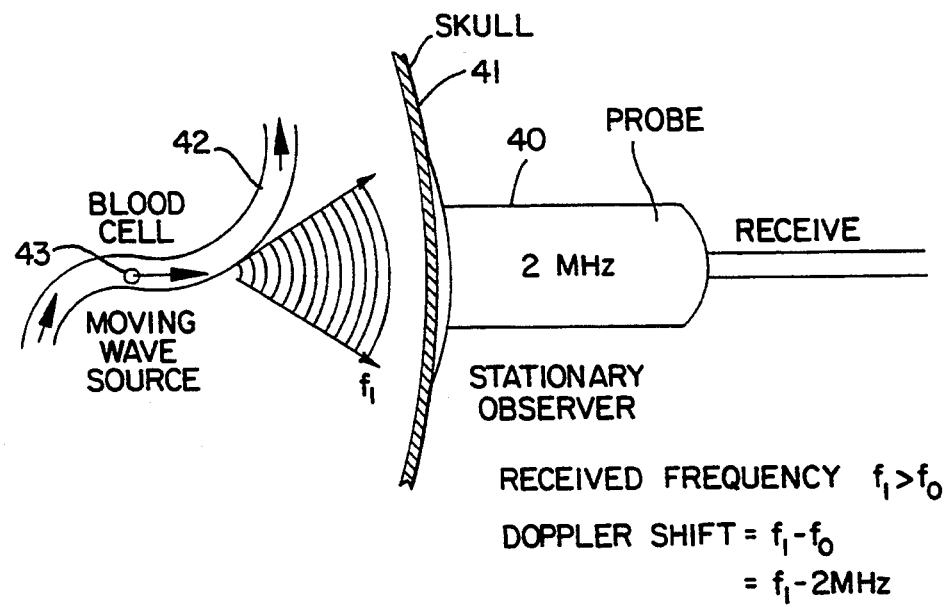
Figure 3:
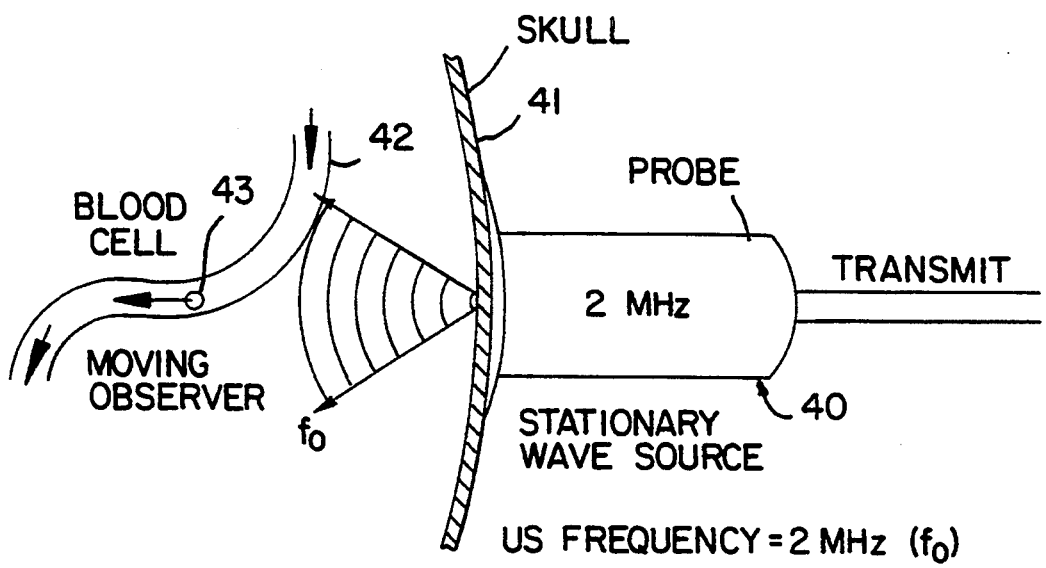
Figure 4:
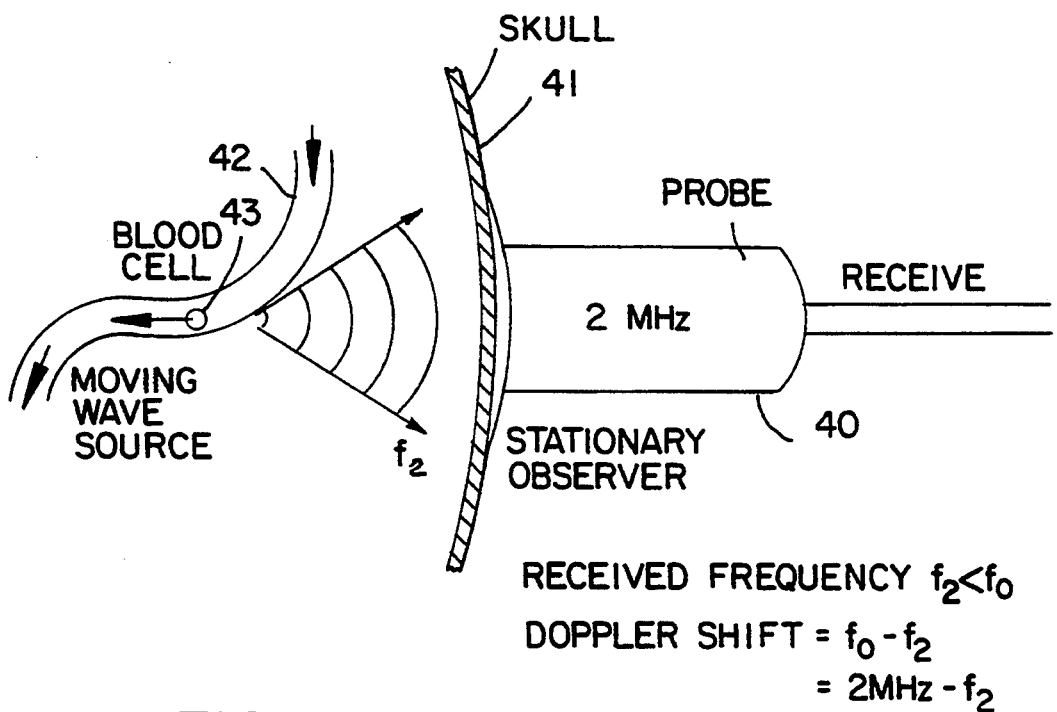
Figure 5:
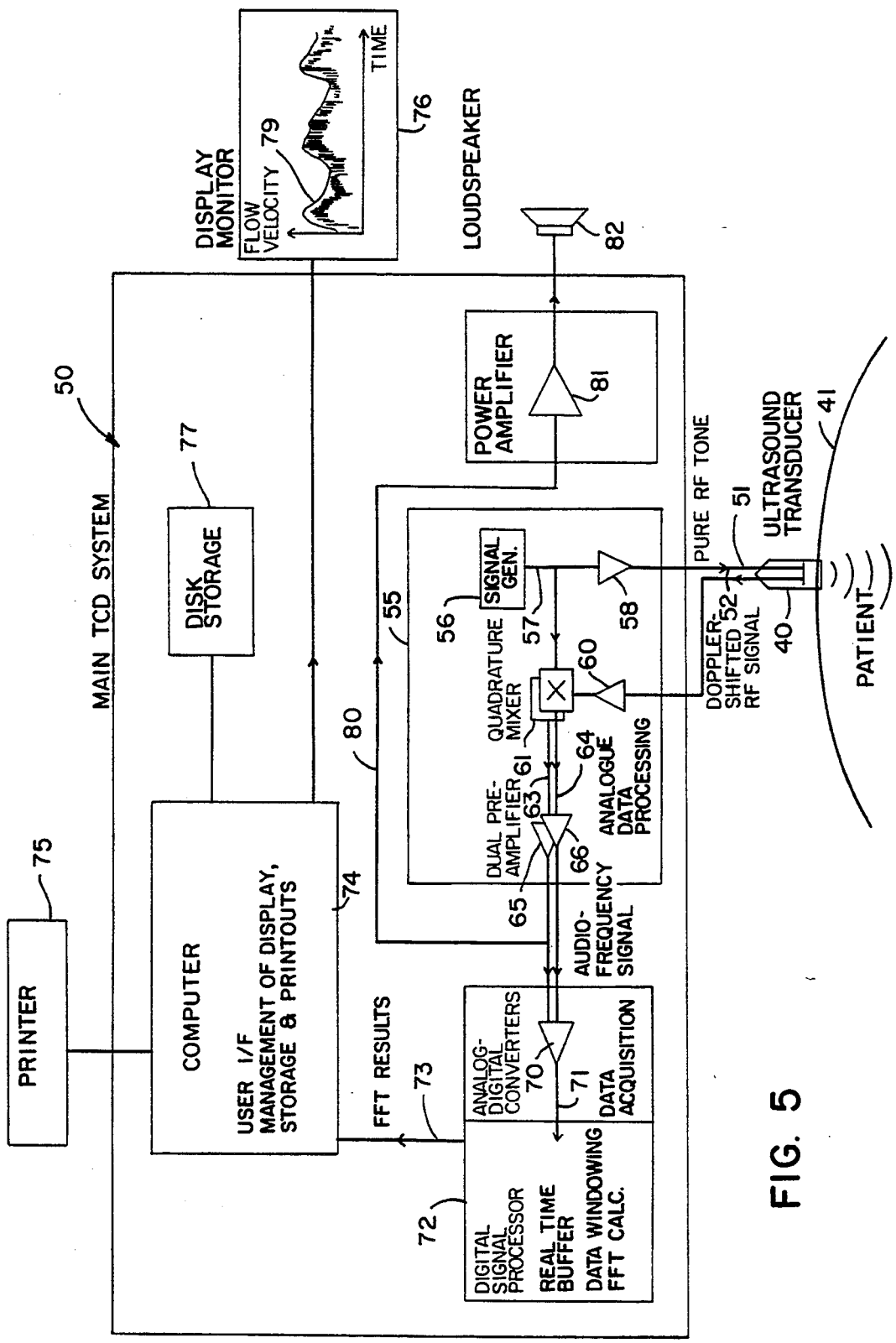
FIG. 5 is a schematic diagram of an apparatus in accordance with the present invention for carrying out transcranial Doppler sonography.
Figure 6:
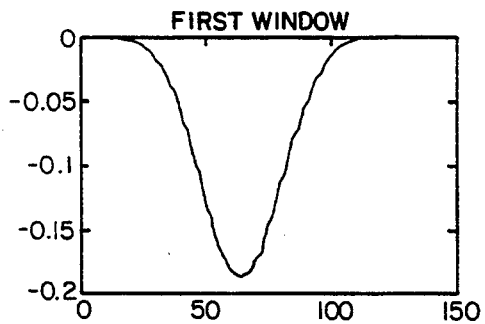
FIGS. 6–9 are graphs showing exemplary first, second, third and fourth data windows in accordance with the present invention utilizing exemplary parameters.
Figure 7:
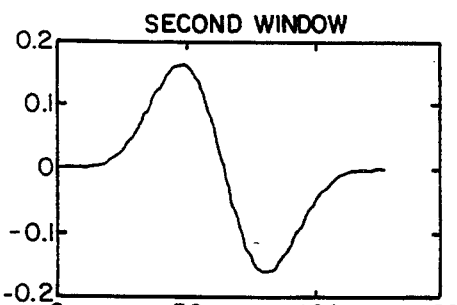
Figure 8:
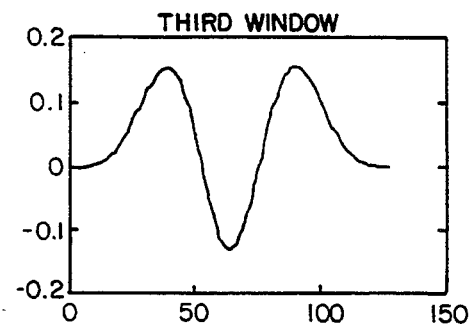
Figure 9:
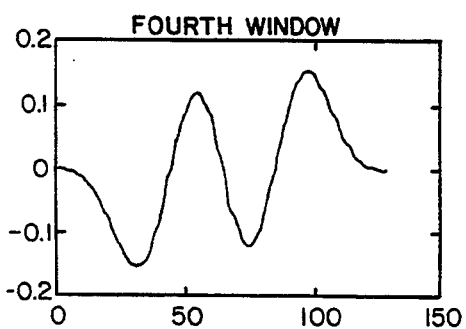
Figure 10:
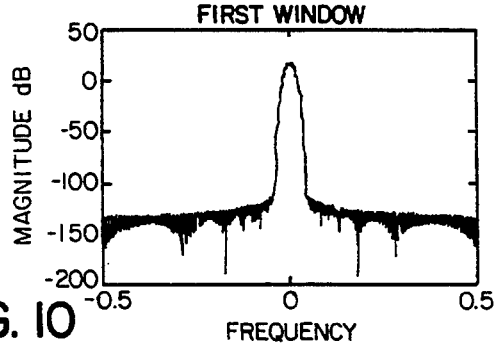
FIGS. 10–13 are graphs showing the frequency responses of the first, second, third and fourth windows of FIGS. 6–9, respectively.
Figure 11:
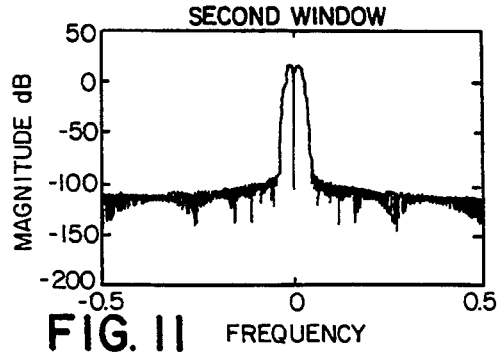
Figure 12:
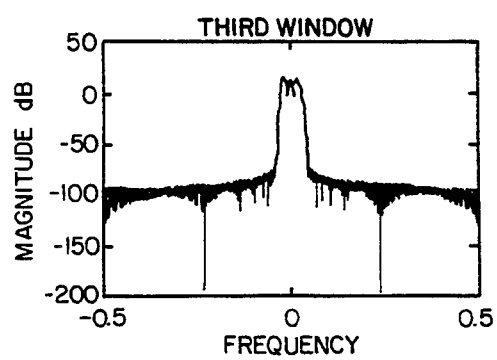
Figure 13:
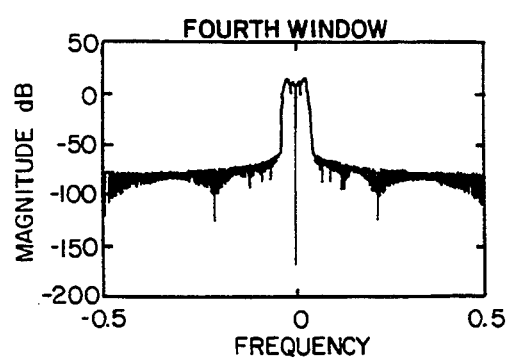

Exemplary apparatus for carrying out the present invention is shown in schematic form generally at 50 in FIG. 5. The apparatus 50 provides pulses of high frequency electrical signal on a line 51 to the probe 40, which puts out pulses of ultrasound, and the Doppler shifted signal from the probe 40 is received on a line 52. The hardware components of the system 50 may be of conventional design, e.g., as used in the TC 2000S Transcranial Doppler System. For purposes of exemplification, the system 50 includes an analog processing section 55 which incorporates a signal generator 56 which provides the drive signal, e.g., pulses of high frequency at 2, 4 or 8 MHz, on an output line 57. The signal from the signal generator on the line 57 is passed through an output driver amplifier 58 to provide the drive signal on the line 51 to the probe 40. The echo signal received from the probe on the line 52 is passed through an input buffer amplifier 60 and then to a quadrature mixer 61 which mixes the received signal with cosine and sine versions of the high frequency input signal provided on a line 57 from the signal generator 56. The two mixed output signals (sine and cosine mixed) from the quadrature mixer 61 are passed on lines 63 and 64 to dual preamplifiers 65 and 66. Conventionally, the preamplifiers 65 and 66 also include low pass filters or integrators to remove the signals at twice the carrier frequency, isolating the audio frequency baseband signal containing the Doppler shifted components which have frequencies in the audio range. The output signals from the amplifiers 65 and 66 are passed on output lines to analog-to-digital converters 70 which provide digital output data on lines 71 to a computer digital signal processor 72 which performs real time buffering and signal processing in accordance with the invention. The output data from the processor 72 are provided on data lines 73 to a computer 74 which manages communications with the user, including display of information through a printer 75 or video display monitor 76, and long term storage of data on a disk storage unit 77. The information displayed on the video monitor 76, and optionally recorded on the printer 75, can take various forms. For purposes of exemplification, a simplified graph of flow velocity distribution versus time is illustrated in FIG. 5 on the face of the display monitor 76. The envelope 79 of the displayed data provides a visual indication to the observer of the relative blood flow velocity from heartbeat to heartbeat, as well as indicating a range of blood flow velocities.

The output of the preamplifier 65 may also be fed on a line 80 to an audio power amplifier 81 which provides its output to a loud speaker 82. The sound from the loud speaker 82 is often helpful to an observer in determining the relative blood flow velocity as a function of time, and also can be useful to a skilled observer in detecting the presence of artifacts, such as the passage of an embolus.

The digital signal processor 72, (e.g., based on a Motorola 56000, 96000, etc. microprocessor) reads the digital data from the analog-to-digital converters 70 to compute a complex discrete Fourier transform, e.g., a fast Fourier transform (FFT). Each transmitted pulse generates one pair (real and imaginery) of data samples, and an FFT can be computed at any time by the digital signal processor 72 using the most recent set of sample pairs, e.g., the most recent 64, 128 or 256 data sample pairs. The calculation of the complex FFT allows the digital signal processor to distinguish between flow towards the probe and flow away from the probe (positive and negative Doppler shifts).

It is noted that a radio frequency (RF) signal from bi-directional flow (from two nearby arteries) has two sidebands. When such a signal is mixed down to the base band, then the two sidebands become overlayed as audio frequencies. The use of the sine and cosine mixers 61 allows basic information about positive and negative Doppler shifts to be preserved in the phase differences between the two channels.

A 128 point complex FFT generates 128 distinct results (there is no mirroring about the Nyquist frequency), or 64 results for negative Doppler shifts and 64 results for positive Doppler shifts. However, it is not possible to distinguish between a positive Doppler shift of 0.75 F (sample frequency) and a negative Doppler shift of 0.25 F.

In accordance with the present invention, the power spectrum of the input data is determined by applying appropriate multiple windows to the input data set, and performing discrete Fourier transforms on the input data using each of the windows. Although a fast Fourier transform (FFT) is a suitable algorithm for calculating the discrete Fourier transform on the windowed data sets, other algorithms for computing the discrete Fourier transform can be used as desired.

The invention estimates spectra as an average of Fourier spectra computed using each of the windows. The windows are chosen so that the spectra from different windows are approximately statistically independent. Hence, the variance of the spectrum is reduced by the averaging process.

Denote the $k$ th element of the $j$ th window $v_j$ (of a total of M windows) as $v_j(k)$, $k = 0, 1, \ldots, N-1$, and let the data set of interest be represented by the sequence $x(k)$, $k = 0, 1, \ldots, N-1$. The multiple window spectrum estimate $S_{MW}(f)$ as a function of the discrete frequency $f$ then is given by $$S_{MW}(f) = \frac{1}{M} \sum_{m=1}^{M} \left| \sum_{k=0}^{N-1} v_m(k) \times (k) e^{-j2\pi fk} \right|^2.$$

That is, the digital signal processor computes the average of the magnitude squared of the M discrete Fourier transforms of the windowed data sets. The well known fast Fourier transform (FFT) algorithm may be used to calculate each discrete Fourier transform. More sophisticated (and more computationally intensive) estimators using the multiple window method may be utilized, if desired.

A variety of methods can be used to design windows that give approximately statistically independent estimates of the spectrum. Different methods are generally obtained by making different assumptions about the shape of the spectrum of the data. Examples of such windows are described in the following publications: (1) "Spectrum Estimation and Harmonic Analysis," *Proc. IEEE*, Vol 70, pp. 1055-1096, September 1982 by D. Thomson; (2) "Estimation of Structured Covariance Matrices and Multiple Window Spectrum Analysis," *IEEE Trans. Acoust Speech Sig. Proc.*, Vol 38, pp. 1467-1472, August 1990 by B. Van Veen and L. Scharf; (3) "Multiple Window Based Minimum Variance Spectrum Estimation for Multidimensional Random Fields," *IEEE Trans. Signal Proc.*, Vol. 40, pp. 578-589, March 1992, by T. Liu and B. Van Veen; (4) "Quadratic Estimators of the Power Spectrum," in *Advances in Spectrum Analysis and Array Processing, Volume I*, (book) 1991, Prentice Hall, Inc., Chap. 1, pp. 1-57 by C. Mullis and L. Scharf; and (5) "Spectral Estimation of Irregularly Sampled Multidimensional Processes by Generalized Prolate Spheroidal Sequences," *IEEE Trans. Acoust Speech Sig. Proc.*, Vol. 36, pp. 1862-1873, December 1988, by T.P. Bronez.

For the present invention, the windows described in the paper by Thomson are preferred. They are derived assuming that the spectrum of the data is approximately constant over a user specified main lobe width 2 B (where B is in Hz normalized on $-0.5 \leq f \leq 0.5$). This assumption is quite reasonable for reasonably small B in the blood flow estimation problem because the distribution of blood velocities (spectrum as a function of frequency) is a smooth function between the minimum and maximum velocities. Another derivation of the Thomson multiple window method is given in *Adaptive Radar Detection and Estimation* (book), 1992, John Wiley & Sons, Inc., Chap. 7, pp. 381-461, "Adaptive Radar Estimation with Thomson's Multiple Window Method", by A. Drosopoulos and S. Haykin.

The user-specified window main lobe width 2 B may be viewed as the resolution limit of the estimator since spectral details that occur on a finer scale cannot be seen in the spectral estimate. The main lobe width 2 B also determines the maximum number of windows that can be averaged. If N is the data record length, then the absolute maximum number of windows that should be used is 2NB, with a practical upper limit of about 2NB −2. The reason for this limit is the sidelobe structure of the windows; while the initial windows have extremely small sidelobes, as one approaches 2NB, the sidelobes become prohibitively large. There is thus a tradeoff in choosing B. As B is increased, the number of windows available for averaging increases and thus the spectral estimate has greater stability. However, it also has poorer resolution. Typical choices for B range from 2/N to 8/N.

The user preferably can choose B from a set of several values (say 2/N, 4/N, 6/N, or 8/N). This choice then determines which set of windows to apply. The user can then specify the number M of windows used (up to a maximum of 2NB−2). Computational restrictions may limit the sweep speed when relatively large numbers of windows are used. Clinical experience may be used to select appropriate choices of B and M under different conditions.

The windows may be determined in accordance with the invention, given B and N, in the following manner. First, construct the N by N matrix Q with entries:

$$Q_{mn} \begin{cases} 2B, & m = n \\ \sin[2\pi B(m-n)]/[\pi(m-n)], & \\ & m, n = 0, 1, \ldots, N-1 \text{ and } m \neq n \end{cases}$$

Let $v_j$ be the eigenvector of Q corresponding to the jth eigenvalue $\lambda_j$ where the eigenvalues are ordered as $1 > \lambda_1 > \lambda_2 > \ldots > \lambda_N > 0$. That is, $v_j$ satisfies the equation $$Qv_j = \lambda_j v_j \quad j = 1, 2, \ldots, N.$$

An alternate, yet equivalent means for obtaining the eigenvector $v_j$ is as the eigenvectors of the N by N tridiagonal matrix $$T_{ij} = \begin{cases} .5i(N-1), & j = i-1 \\ [.5(N-1) - i]^2 \cos 2\pi B, & j = i \\ .5(i+1)(N-1-i), & j = i+1 \\ 0, & \text{otherwise} \end{cases}$$

Here, $v_j$ is the eigenvector corresponding to the eigenvalues $\theta_j$ where $\theta_1 > \theta_2 > \ldots > \theta_N$. Note that the eigenvalues of T and Q are different, although the eigenvectors are the same. Tridiagonal eigensystems (T) are often easier to solve and numerically more accurate, depending on the software used. The eigenvectors, which constitute the data window functions in accordance with the invention, may be precomputed and stored in the digital signal processor 72 memory or on a disk.

It can be shown that for large N, the first 2NB eigenvalues of Q are approximately one and the remainder approximately zero. The value of $\lambda_j$ determines the relative energy in the main lobe of the discrete Fourier transform of $v_j$. The $v_j$ are orthonormal, so by Parseval's theorem the total energy in the frequency domain is one. The energy in the band $-B < f < B$ is given by $\lambda_j$, while the energy outside this band is given by $1 - \lambda_j$. Hence, the closer $\lambda_j$ is to unity, the smaller the sidelobes of the window.

As an example, the matrix Q may be calculated for N=128 and B=0.04. The first eleven eigenvalues of Q are:

0.99999999999973

0.99999999996621

0.99999999801957

0.99999992713353

0.99999812024196

0.99996408773636

0.99947851161881

0.99424348578675

0.95402011211963

0.77042212402441

0.39555542868194

The first four time window functions, the eigenvectors of Q (or T), are plotted in FIGS. 6–9, respectively. It should be noted that the polarity of the window functions is arbitrary. The frequency responses of the first, second, third and fourth window functions are shown in FIGS. 10–13, respectively.

The following describes a sequence of experiments comparing the conventional single FFT and multiple window (MW) signal processing methods for computing Doppler spectra from transcranial Doppler (TCD) data. The results are illustrated in FIGS. 14–17. The signal processing for both approaches is implemented in the digital signal processor 72.

Figure 18:
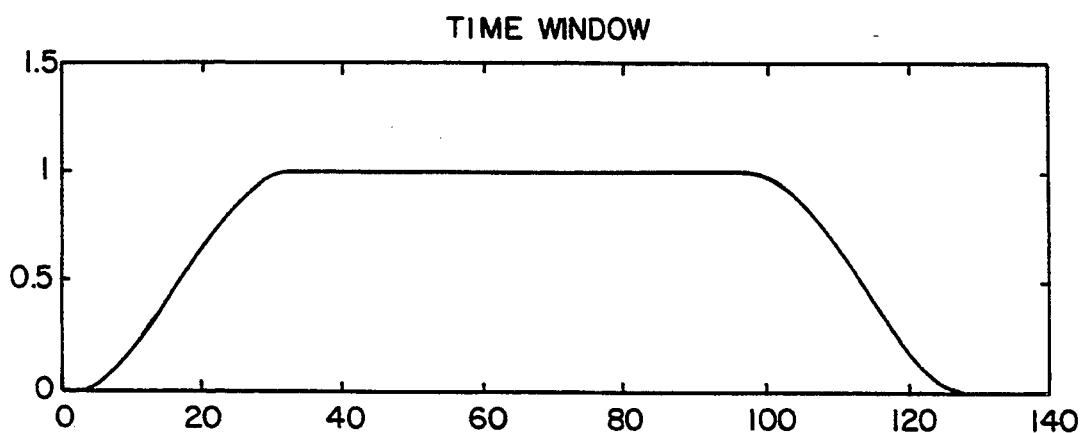
FIG. 18 is a graph showing the window used in the conventional signal processing of FIGS. 14 and 16.
Figure 19:
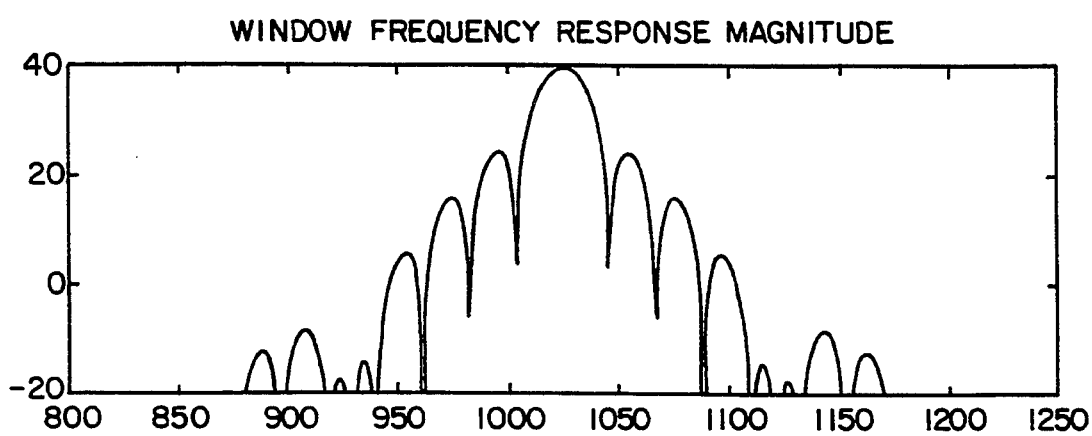
FIG. 19 is a graph showing the frequency response of the window of FIG. 18.

Digitized TCD records sampled at a 6 kHz pulse repetition frequency (PRF) containing about 16 thousand points each from a normal subject are analyzed. Records are collected at good SNR and at poor SNR. The depth is 50 mm into the head of the subject. Each 16 k data record is segmented into 127 records of 128 points. A conventional 128 point FFT of each 128 point data record is computed and converted to magnitude in dB using the window shown in FIG. 18. The first and last 32 points in the window function are ½ a sine wave. The frequency response of this window in FIG. 19 shows the first sidelobe is down 15 dB, and the first null at 0.01 in normalized frequency.

The method in accordance with the invention utilized an average of 5 eigenspectra windows computed using each 128 point record with B=0.04, and thus 2NB≈10. An FFT algorithm was then used on the windowed data for each set, and the averaged power spectrum for that data is determined as described above.

Figure 14:
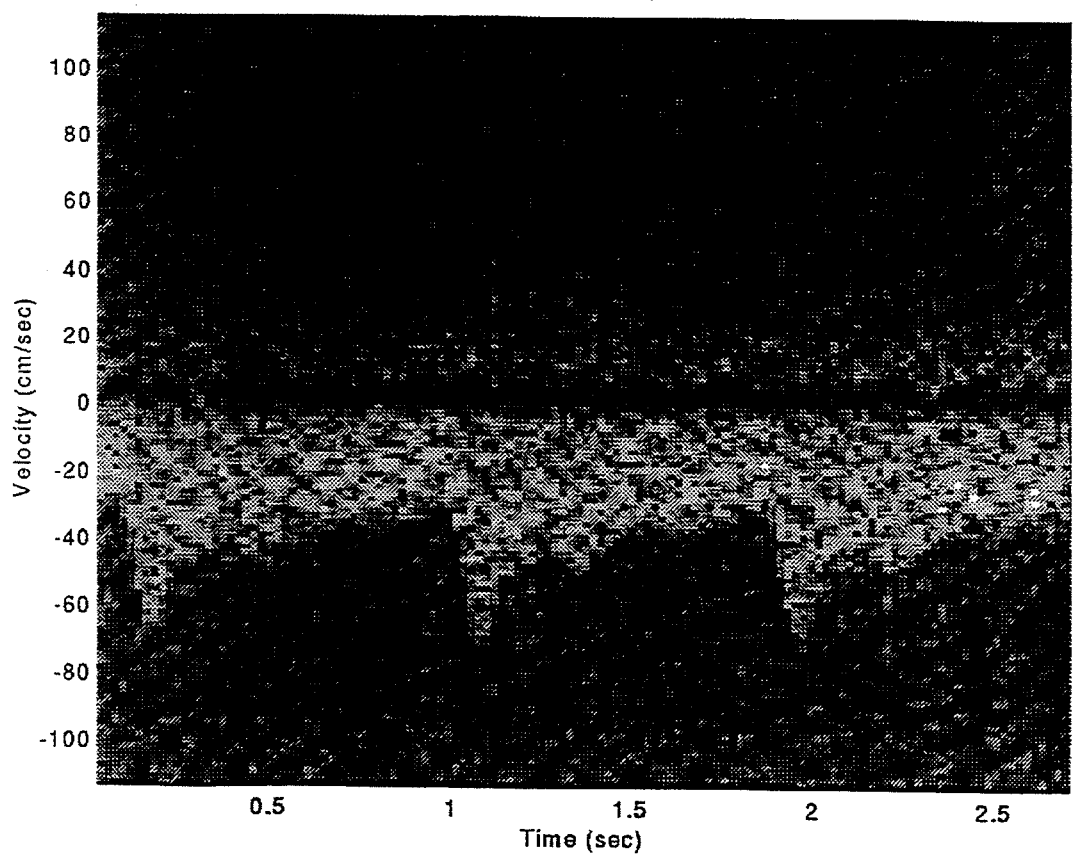
FIG. 14 is an exemplary spectral sonogram map showing results obtained with conventional FFT signal processing and a normal signal to noise ratio.
Figure 15:
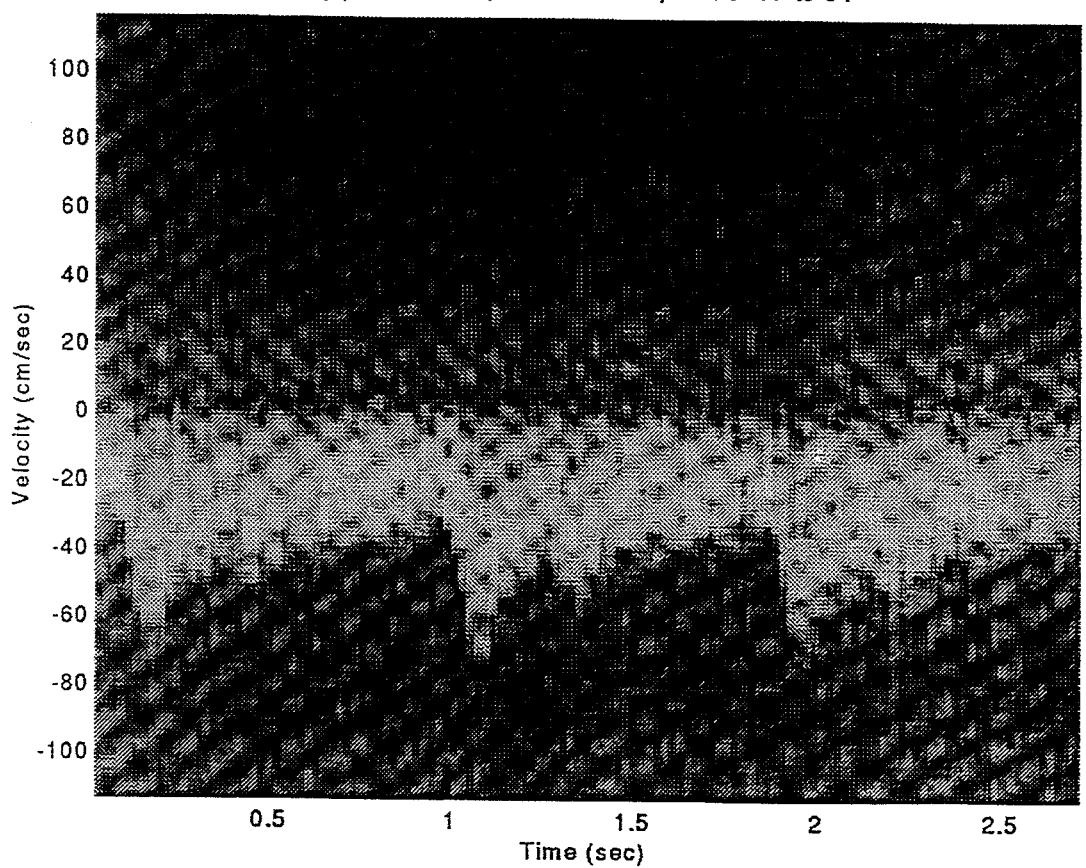
FIG. 15 is an exemplary spectral sonogram map showing results obtained with the present invention and a normal signal to noise ratio.

The estimate of the spectrum from each 128 point record is displayed as a vertical line on the maps of FIGS. 14–17 which are provided herein for illustrative purposes only. Commonly, these maps would be displayed to an operator in color to aid in communicating information to the user. Each map contains 127 vertical lines (127*128≈16 k). The horizontal axis represents line number and thus corresponds to time. The vertical axis is frequency (or velocity) with the zero frequency (zero velocity) point at 64. The corresponding frequency range is from −3000 Hz to 3000 Hz. The range in dB associated with the spectral amplitudes in each map is noted as scale in each title in the figures. FIGS. 14 and 15 show the results with normal signal to noise ratio (SNR). Results with a conventional FFT approach are shown in FIG. 14 (scaling from −17 to 64), and results on the same data with the present invention are shown in FIG. 15 (scaling from −17 to 64).

Figure 16:
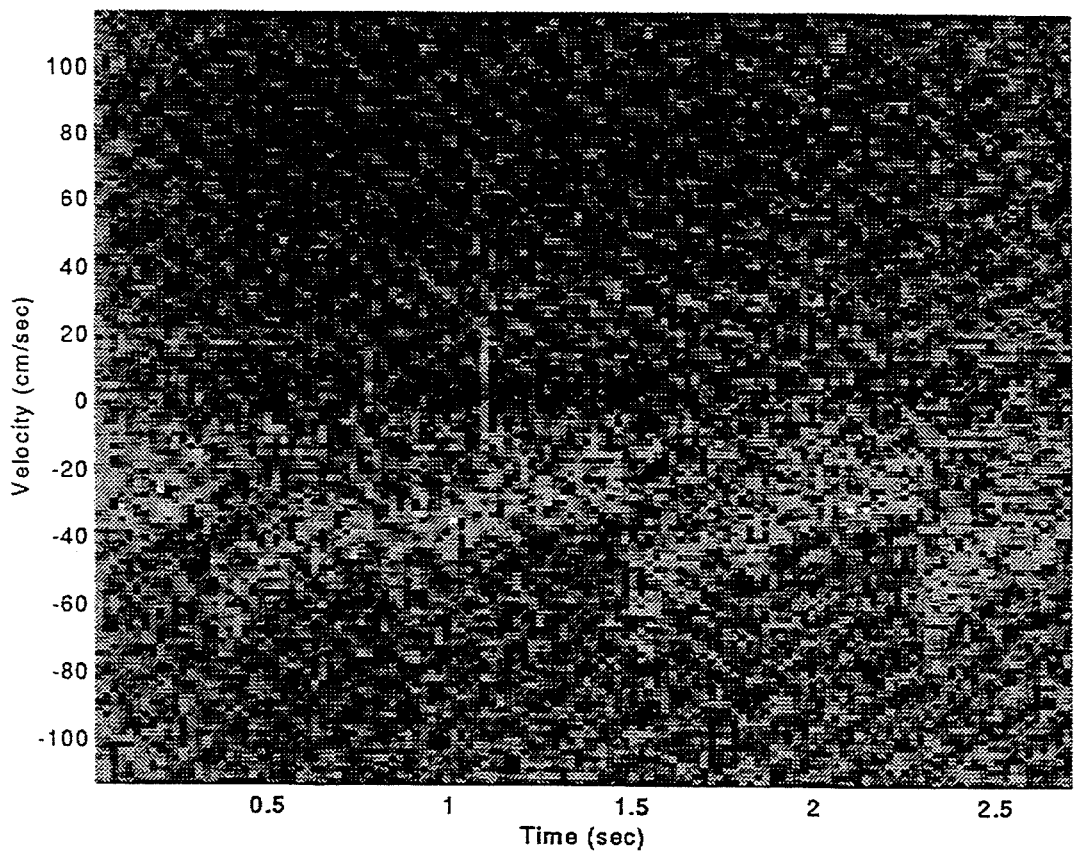
FIG. 16 is an exemplary spectral sonogram map showing results obtained with conventional FFT signal processing and a poor signal to noise ratio.
Figure 17:
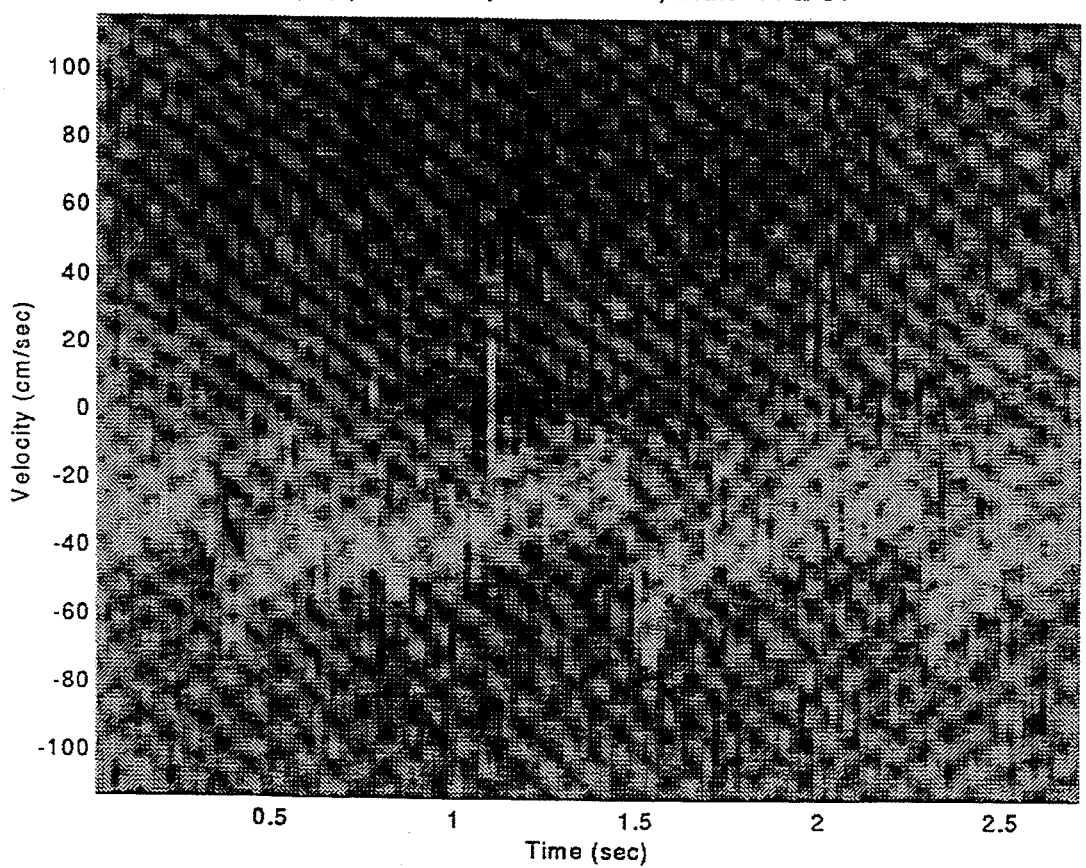
FIG. 17 is an exemplary spectral sonogram map showing results obtained with the present invention and a poor signal to noise ratio.

FIGS. 16 and 17 show the results with a poor SNR. Results with a conventional FFT are shown in FIG. 16 (scaling from −14 to 51). Results on the same data with the present invention are shown in FIG. 17 (scaling from −14 to 51).

A primary advantage of the present invention is that it reduces the variability in the spectral estimate. This helps an observer distinguish the Doppler signal from noise in the spectral display. Theory predicts that the variance of the FFT spectrum is proportional to the square of the spectrum (for any window), and the present invention reduces variance by a factor of M, if M windows are used. The variance reduction is evident in the maps of FIGS. 14–17. The conventional FFT method generally has much greater dynamic range because it has much greater variance.

The present invention requires that M discrete Fourier transforms of windowed data be averaged. The M window functions can be computed before data acquisition, and then stored in memory. In most of the data presented above, five 128 point FFT's are averaged to get each spectral amplitude function (one vertical slice of a map).

It is understood that the invention is not confined to the particular embodiments set forth herein as illustrative, but encompasses all such modified forms thereof as come within the scope of the following claims.

What is claimed is:

1. A method for carrying out Doppler sonography on a subject comprising the steps of:
    (a) applying a pulse of ultrasound to the subject;
    (b) measuring the received ultrasound signal and providing a corresponding received electrical signal;
    (c) isolating the Doppler frequency components from the received signal;
    (d) sampling the isolated Doppler frequency components to provide digital data corresponding to the sample;
    (e) repeating the foregoing steps to provide a set of data for a selected number of samples;
    (f) determining a power spectrum for the data set by providing multiple window functions for the data set, the window functions determined so that the spectra computed using different windows are approximately statistically independent, applying each of the window functions to the data set to provide windowed data sets and determining a discrete Fourier transform for each of the windowed data sets, and determining the power spectrum as the averaged sum of the squares of the magnitudes of each of the discrete Fourier transforms of the windowed data sets;
    (g) repeating the foregoing steps to provide a power spectra as a function of time.

2. The method of claim 1 including the step of displaying to an operator the power spectra as a function of time.

3. The method of claim 1 wherein the step of determining the power spectrum $S_{MW}(f)$ as a function of the discrete frequency f is carried out by evaluating the expression:

$$S_{MW}(f) = \frac{1}{M} \sum_{m=1}^{M} \left| \sum_{k=0}^{N-1} v_m(k) \times (k) e^{-j2\pi fk} \right|^2,$$

where M is the number of window functions applied to the data sets, $v_j(k)$ is the k th element of the j th window function, x(k) is the k th element of the data set, k=0, 1, 2, ..., N−1, and N is the number of samples in the data set.

4. The method of claim 3 wherein the step of providing multiple window functions for the data set provides window functions which are the eigenvectors $v_j$ of the matrix Q having entries $Q_{mn}$ determined as follows:

$$Q_{mn} \begin{cases} 2B, \\ \sin[2\pi B(m-n)]/[\pi(m-n)], \\ \quad m = n \\ m, n = 0, 1, \ldots, N-1 \text{ and } m \neq n \end{cases}$$

where B is a selected number.

5. The method of claim 4 wherein B is a number from 2/N to 8/N.

6. The method of claim 3 wherein the step of providing multiple window functions for the data set provides window functions which are the eigenvectors $v_j$ of the matrix T having entries determined as follows:

$$T_{ij} = \begin{cases} .5i(N-1), j = i - 1 \\ [.5(N-1) - i]^2 \cos 2\pi B, j = i \\ .5(i+1)(N-1-i), j = i + 1 \\ 0, \text{ otherwise} \end{cases}$$

where B is a selected number.

7. The method of claim 6 wherein B is a number from 2/N to 8/N.

8. Apparatus for Doppler sonography comprising:
(a) an ultrasound transducer for providing ultrasound pulses to a subject and for receiving ultrasound echoes from the subject and providing a received signal corresponding thereto;
(b) an ultrasound signal generator generating pulses of electrical signal at an ultrasound frequency connected to provide such pulses to the ultrasound transducer;
(c) means connected to the ultrasound transducer for isolating the Doppler frequency components from the received signal from the ultrasound transducer;
(d) an analog-to-digital converter connected to the means for isolating the Doppler frequency components to convert the components to digital data corresponding to the sample;
(e) digital processing means for receiving the digital data corresponding to the samples from the analog-to-digital converter and for determining a power spectrum for the data set obtained from a selected number of samples comprising a data set corresponding to a selected number of pulses of ultrasound provided to a subject including means for providing multiple window functions for the data set, the window functions determined so that the spectra computed using different windows are approximately statistically independent, means for applying each of the window functions to the data set to provide windowed data sets and for determining a discrete Fourier transform for each of the windowed data sets, and for determining the power spectrum as the averaged sum of the squares of the magnitudes of each of the discrete Fourier transforms of the windowed data sets, and for determining the power spectrum for new sets of data corresponding to a selected number of samples over a period of time to provide a power spectra as a function of time.

9. The apparatus of claim 8 including means for displaying to an operator the power spectra as a function of time.

10. The apparatus of claim 8 wherein the means for determining the power spectrum $S_{MW}(f)$ as a function of the discrete frequency f does so by evaluating the expression:

$$S_{MW}(f) = \frac{1}{M} \sum_{m=1}^{M} \left| \sum_{k=0}^{N-1} v_m(k) \times (k) e^{-j2\pi fk} \right|^2,$$

where M is the number of window functions applied to the data sets, $v_j(k)$ is the k th element of the j th window function, x(k) is the k th element of the data set, k=0, 1, 2, ..., N−1, and N is the number of samples in the data set.

11. The apparatus of claim 10 wherein the means for providing multiple window functions for the data set provides window functions which are the eigenvectors $v_j$ of the matrix Q having entries $Q_{mm}$ determined as follows:

$$Q_{mn} \begin{cases} 2B, \\ \sin[2\pi B(m-n)]/[\pi(m-n)], \\ \quad m = n \\ m, n = 0, 1, \ldots, N-1 \text{ and } m \neq n \end{cases}$$

where B is a selected number.

12. The apparatus of claim 11 wherein B is a number from 2/N to 8/N.

13. The apparatus of claim 12 wherein the means for providing multiple window functions for the data set provides window functions which are the eigenvectors $v_j$ of the matrix T having entries determined as follows:

$$T_{ij} = \begin{cases} .5i(N-1), j = i - 1 \\ [.5(N-1) - i]^2 \cos 2\pi B, j = i \\ .5(i+1)(N-1-i), j = i + 1 \\ 0, \text{ otherwise} \end{cases}$$

where B is a selected number.

* * * * *

UNITED STATES PATENT AND TRADEMARK OFFICE
CERTIFICATE OF CORRECTION

PATENT NO. : 5,379,770
DATED : January 10, 1995
INVENTOR(S) : Barry D. Van Veen

It is certified that error appears in the above-indentified patent and that said Letters Patent is hereby corrected as shown below:

In column 4, lines 19-24 of the patent, the equation should read as follows after line 4):

$$Q_{mn} = \begin{cases} 2B, & m=n \\ \sin[2\pi B(m-n)]/[\pi(m-n)], & m,n=0,1,\ldots,N-1 \text{ and } m\neq n \end{cases}$$

In column 8, lines 9-14 of the patent, the equation should read as follows $$Q_{mn} = \begin{cases} 2B, & m=n \\ \sin[2\pi B(m-n)]/[\pi(m-n)], & m,n=0,1,\ldots,N-1 \text{ and } m\neq n \end{cases}$$

In column 10, line 68 of the patent, "$Q_{mm}$" should be --$Q_{mn}$--

In column 11, lines 1-7 of the patent, the equation should read as follows $$Q_{mn} = \begin{cases} 2B, & m=n \\ \sin[2\pi B(m-n)]/[\pi(m-n)], & m,n=0,1,\ldots,N-1 \text{ and } m\neq n \end{cases}$$

In column 12, line 29 of the patent, "$Q_{mm}$" should be --$Q_{mn}$--

UNITED STATES PATENT AND TRADEMARK OFFICE
CERTIFICATE OF CORRECTION

PATENT NO. : 5,379,770
DATED : January 10, 1995
INVENTOR(S) : Barry D. Van Veen

It is certified that error appears in the above-indentified patent and that said Letters Patent is hereby corrected as shown below:

In column 12, lines 31-36 of the patent, the equation should read as follows $$Q_{mn} = \begin{cases} 2B, & m=n \\ \sin[2\pi B(m-n)]/[\pi(m-n)], & m,n=0,1,\ldots,N-1 \text{ and } m \neq n \end{cases}$$

Signed and Sealed this

Fourth Day of June, 1996

Attest:

BRUCE LEHMAN

*Attesting Officer*    Commissioner of Patents and Trademarks